US012595259B2

(12) United States Patent
Li et al.

(10) Patent No.: US 12,595,259 B2
(45) Date of Patent: Apr. 7, 2026

(54) AMINOPYRIDINE COMPOUND

(71) Applicant: ZHUHAI UNITED LABORATORIES CO., LTD., Guangdong (CN)

(72) Inventors: Peng Li, Shanghai (CN); Chong Su, Guangdong (CN); Xiaolin Li, Shanghai (CN); Zhi Luo, Shanghai (CN); Haiying He, Shanghai (CN); Guoping Hu, Shanghai (CN); Jian Li, Shanghai (CN); Shuhui Chen, Shanghai (CN)

(73) Assignee: ZHUHAI UNITED LABORATORIES CO., LTD., Guangdong (CN)

( * ) Notice: Subject to any disclaimer, the term of this patent is extended or adjusted under 35 U.S.C. 154(b) by 578 days.

(21) Appl. No.: 18/000,684

(22) PCT Filed: Jun. 17, 2021

(86) PCT No.: PCT/CN2021/100689

§ 371 (c)(1),
(2) Date: Dec. 5, 2022

(87) PCT Pub. No.: WO2021/254453

PCT Pub. Date: Dec. 23, 2021

(65) Prior Publication Data

US 2023/0174524 A1 Jun. 8, 2023

(30) Foreign Application Priority Data

Jun. 17, 2020 (CN) ......................... 202010554404.0

(51) Int. Cl.

| | |
|---|---|
| ***C07D 213/74*** | (2006.01) |
| ***A61K 31/4412*** | (2006.01) |
| ***A61K 31/4418*** | (2006.01) |
| ***A61K 31/443*** | (2006.01) |
| ***A61K 31/4436*** | (2006.01) |
| ***A61K 31/4439*** | (2006.01) |
| ***A61K 31/444*** | (2006.01) |
| ***A61P 27/00*** | (2006.01) |
| ***A61P 27/04*** | (2006.01) |
| ***C07D 401/04*** | (2006.01) |
| ***C07D 401/06*** | (2006.01) |
| ***C07D 401/12*** | (2006.01) |
| ***C07D 407/04*** | (2006.01) |
| ***C07D 409/04*** | (2006.01) |
| ***C07D 413/04*** | (2006.01) |
| ***C07D 417/04*** | (2006.01) |

(52) U.S. Cl.
CPC ............ *C07D 417/04* (2013.01); *A61P 27/04* (2018.01)

(58) Field of Classification Search
CPC .. C07D 213/74; C07D 401/04; C07D 401/06; C07D 401/12; C07D 407/04; C07D 409/04; C07D 413/04; C07D 417/04; A61K 31/443; A61K 31/4436; A61K 31/4439; A61K 31/444; A61K 31/4418; A61K 31/4412; A61P 27/00; A61P 27/04
See application file for complete search history.

(56) References Cited

U.S. PATENT DOCUMENTS

| | | | |
|---|---|---|---|
| 9,650,342 | B2 | 5/2017 | Jordan et al. |
| 2018/0250306 | A1 | 9/2018 | Brady et al. |
| 2022/0127243 | A1 | 4/2022 | Li et al. |

FOREIGN PATENT DOCUMENTS

| | | | | |
|---|---|---|---|---|
| CN | 101321742 A | 12/2008 | | |
| CN | 108135867 A | 6/2018 | | |
| WO | 2018039197 A1 | 3/2018 | | |
| WO | 2019075136 A1 | 4/2019 | | |
| WO | WO-2020125659 A1 * | 6/2020 | ............. | A61K 31/44 |

OTHER PUBLICATIONS

May 27, 2024 Chinese Office Action issued in Chinese Patent Application No. 202180042872.2.
Sep. 16, 2021 International Search Report issued in International Patent Application No. PCT/CN2021/100689.
Sep. 16, 2021 Written Opinion of the International Searching Authority issued in International Patent Application No. PCT/CN2021/100689.
Chinese patent No. CN2020105544040(not published), 2020.

* cited by examiner

*Primary Examiner* — Brenda L Coleman
(74) *Attorney, Agent, or Firm* — Houston Beshining Law Office PLLC; Liangang Ye

(57) ABSTRACT

An aminopyridine compound that may be used as an aldehyde trapping agent, and specifically disclosed is a compound represented by formula (I) and a pharmaceutically acceptable salt thereof.

(I)

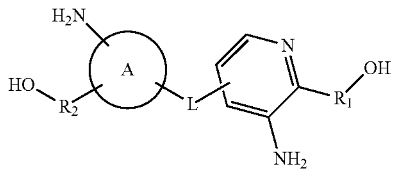

18 Claims, 1 Drawing Sheet

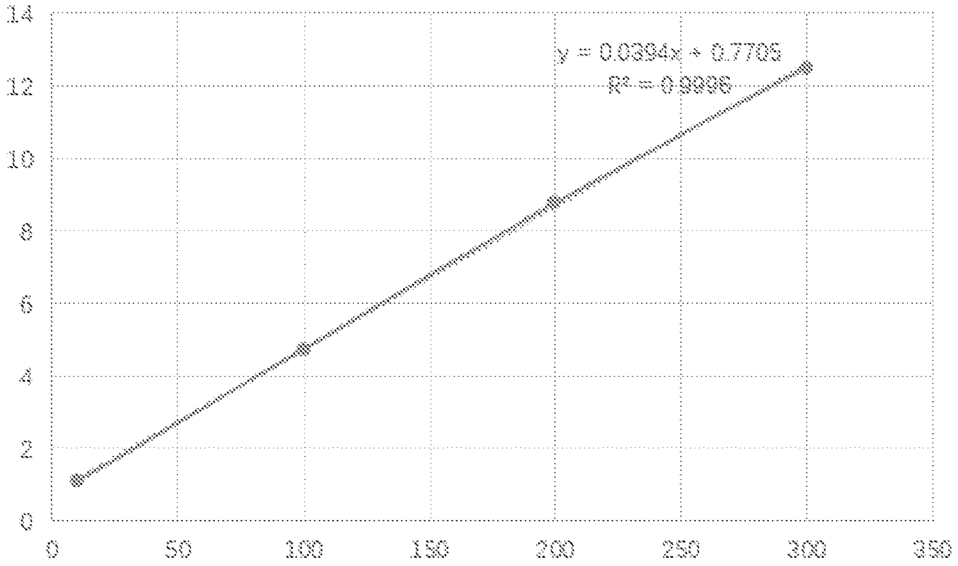
y = 0.0394x + 0.7705
R² = 0.9996
14
12
10
8
6
4
2
0
0
50
100
150
200
250
300
350

AMINOPYRIDINE COMPOUND

The present application is a National Stage of International Application No. PCT/CN2021/100689, filed on Jun. 17, 2021, which claims the priority of the Chinese Patent Application NO. CN202010554404.0 filed on Jun. 17, 2020.

TECHNICAL FIELD

The present disclosure relates to a new aminopyridine compound, in particular to a compound represented by formula (I) and a pharmaceutically acceptable salt thereof.

BACKGROUND

Xerophthalmia, also known as keratoconjunctivitis sicca, is a general term for a variety of diseases caused by any reason, such as abnormal tear quality or quantity or abnormal tear kinetics, and a decrease in the stability of the tear film accompanied by features of eye discomfort (or) ocular surface tissue lesions. Specific symptoms of discomfort are: eye irritation, visual disturbance and tear film instability. Some of these syndromes are caused by inflammation of the ocular surface, resulting in loss of lacrimal gland function. In addition, it is also associated with systemic autoimmunity.

Some toxic aldehydes, such as malondialdehyde (MDA), 4-hydroxy-2-nonenal (4HNE), are produced by the body or ocular tissues and organs through metabolic mechanisms, etc., and these aldehydes are highly reacted with proteins, carbohydrates, oils and DNA, leading to chemical modification of biomolecules and activation of inflammatory molecular regulators such as NF-kappaB, thus causing damage to different organs, which is one of the causes of xerophthalmia.

In the present disclosure, through research, a small-molecule drug enters an ocular inflammation site in the form of eye drops or oral administration, and through a complex reaction with aldehyde in vivo to reduce the toxicity of the aldehyde, reduce the inflammation, and achieve the effect of treating xerophthalmia.

CONTENT OF THE PRESENT INVENTION

The present disclosure provides a compound represented by formula (I) or a pharmaceutically acceptable salt thereof, (I)

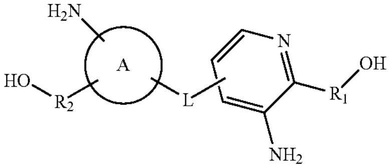

wherein,

L is selected from —O— and —$(CR_4R_5)_n$—;

$R_1$ is selected from —$C_{1-6}$ alkyl- and —$C_{3-5}$ cycloalkyl-, and the —$C_{1-6}$ alkyl- and —$C_{3-5}$ cycloalkyl- are optionally substituted by 1, 2 or 3 $R_a$;

ring A is selected from phenyl, pyridyl and 5-membered heteroaryl, and the phenyl, pyridyl and 5-membered heteroaryl are optionally substituted by 1, 2 or 3 $R_3$;

and when ring A is selected from phenyl and pyridyl, then $R_2$ is selected from —$C_{5-6}$ alkyl- and —$C_{3-5}$ cycloalkyl-, and the —$C_{5-6}$ alkyl- and —$C_{3-5}$ cycloalkyl- are optionally substituted by 1, 2 or 3 $R_b$;

when ring A is selected from 5-membered heteroaryl, then $R_2$ is selected from —$C_{1-6}$ alkyl- and —$C_{3-5}$ cycloalkyl-, and the —$C_{1-6}$ alkyl- and —$C_{3-5}$ cycloalkyl- are optionally substituted by 1, 2 or 3 $R_c$;

$R_3$ is selected from H, F, Cl, Br, I and $CH_3$;

$R_4$ and $R_5$ are each independently selected from H and $CH_3$;

n is selected from 0, 1 and 2;

$R_a$, $R_b$ and $R_c$ are each independently selected from F, Cl, Br and I;

the "5-membered heteroaryl" comprises 1, 2, 3 or 4 heteroatoms or heteroatom groups independently selected from —O—, —NH—, —S— and N, respectively.

In some embodiments of the present disclosure, the $R_1$ is selected from $CH_2$, $C(CH_3)_2$, $C(CH_2CH_3)_2$, cyclopropyl and cyclobutyl, and the $CH_2$, $C(CH_3)_2$, $C(CH_2CH_3)_2$, cyclopropyl and cyclobutyl are optionally substituted by 1, 2 or 3 $R_a$, and other variables are as defined in the present disclosure.

In some embodiments of the present disclosure, the $R_1$ is selected from $C(CH_3)_2$, $C(CH_2CH_3)_2$, cyclopropyl and cyclobutyl, and other variables are as defined in the present disclosure.

In some embodiments of the present disclosure, when the ring A is selected from phenyl and pyridyl, then $R_2$ is selected from $C(CH_2CH_3)_2$, cyclopropyl and cyclobutyl, and other variables are as defined in the present disclosure.

In some embodiments of the present disclosure, when the ring A is selected from 5-membered heteroaryl, then $R_2$ is selected from $C(CH_3)_2$, $C(CH_2CH_3)_2$, cyclopropyl and cyclobutyl, and other variables are as defined in the present disclosure.

In some embodiments of the present disclosure, the L is selected from a single bond, —O—, $CH_2$ and —$CH_2CH_2$—, and other variables are as defined in the present disclosure.

In some embodiments of the present disclosure, the ring A is selected from phenyl, pyridyl, pyrrolyl, furyl, thienyl, oxazolyl and thiazolyl, and the phenyl, pyridyl, pyrrolyl, furyl, thienyl, oxazolyl and thiazolyl are optionally substituted by 1, 2 or 3 $R_3$, and other variables are as defined in the present disclosure.

In some embodiments of the present disclosure, the ring A is selected from phenyl, pyridyl, pyrrolyl, furyl, thienyl and oxazolyl, and the phenyl, pyridyl, pyrrolyl, furyl, thienyl and oxazolyl are optionally substituted by 1, 2 or 3 $R_3$, and the other variables are as defined in the present disclosure.

In some embodiments of the present disclosure, the ring A is selected from

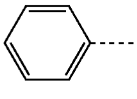, 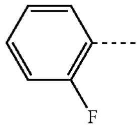, 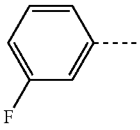,

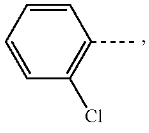, 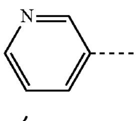, 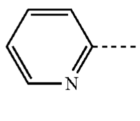,

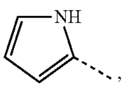, 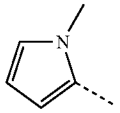, 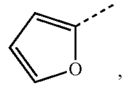, 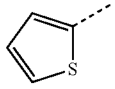,

-continued

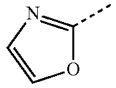 and 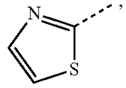, and other variables are as defined in the present disclosure.

In some embodiments of the present disclosure, the ring A is selected from

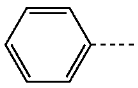, 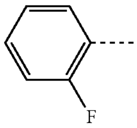, 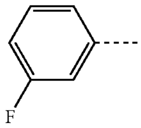,

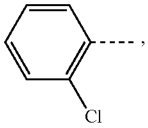, 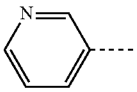, 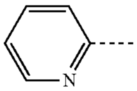,

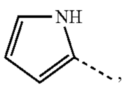, 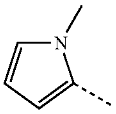, 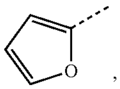, 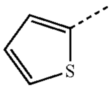 and

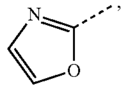, and other variables are as defined in the present disclosure.

In some embodiments of the present disclosure, the structural unit

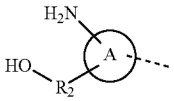

is selected from

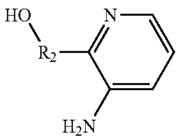, 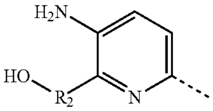,

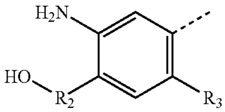, 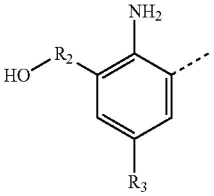,

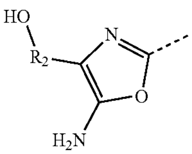, 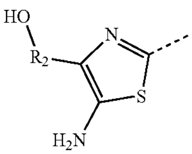,

-continued

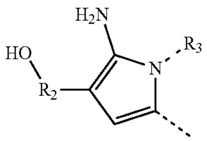, 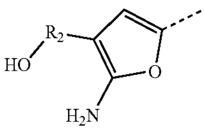 and

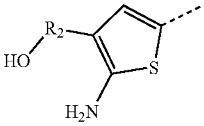, and other variables are as defined in the present disclosure.

In some embodiments of the present disclosure, the structural unit

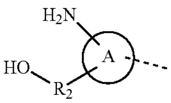

is selected from

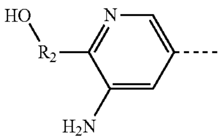, 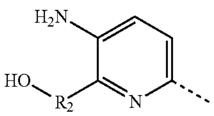,

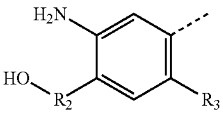, 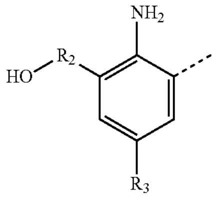,

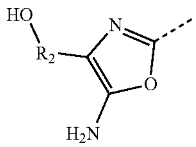, 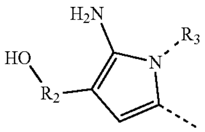,

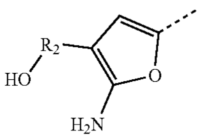 and 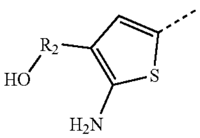, and other variables are as defined in the present disclosure.

In some embodiments of the present disclosure, the structural unit

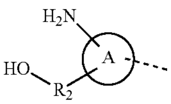

is selected from
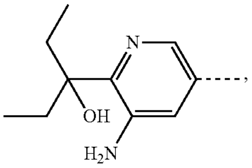,
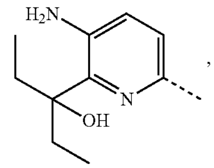,
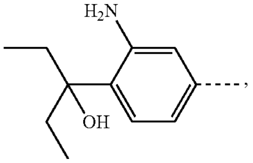,
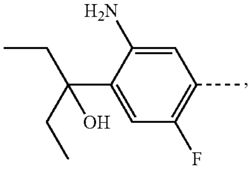,
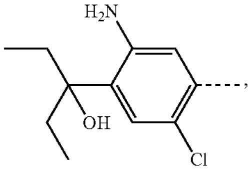,
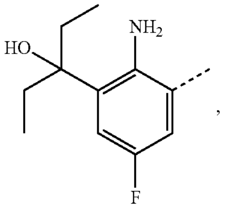,
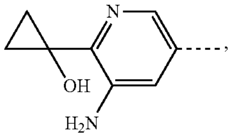,
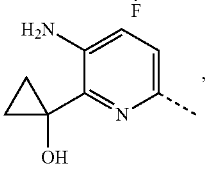,
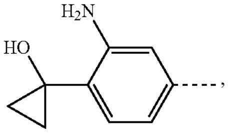,
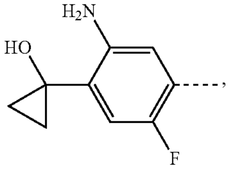,
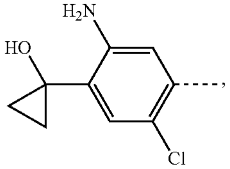,
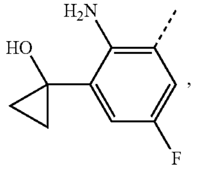,
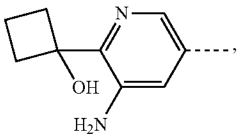,
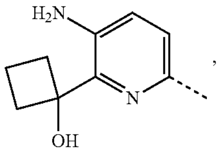,
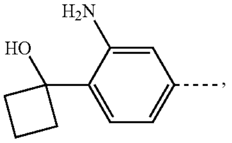,
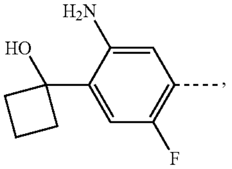,
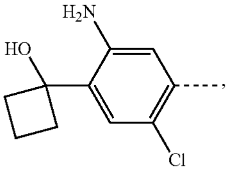,
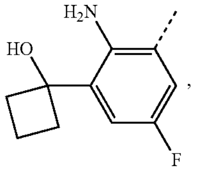,
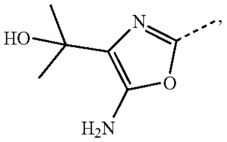,
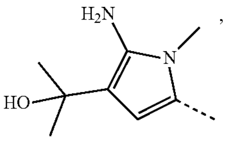,
-continued
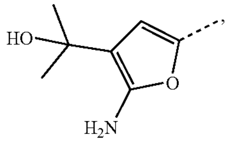,
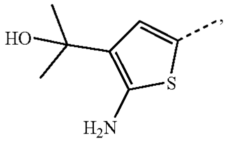,
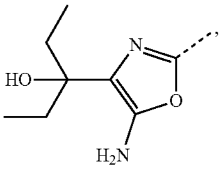,
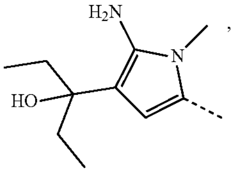,
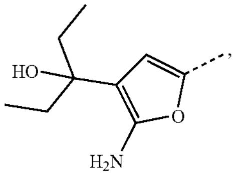,
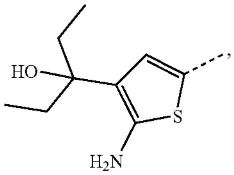,
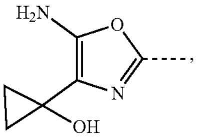,
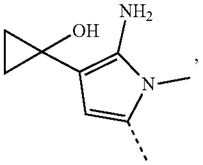,
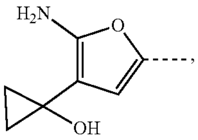,
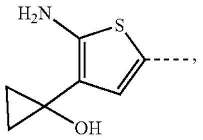,
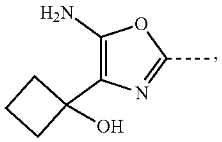,
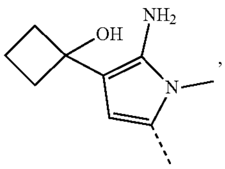,
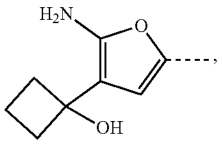,
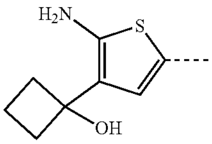 and
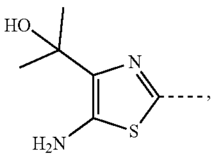,
and other variables are as defined in the present disclosure.
In some embodiments of the present disclosure, the structural unit
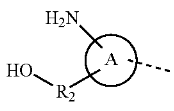

is selected from
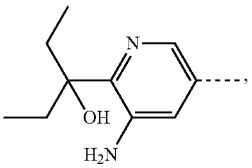
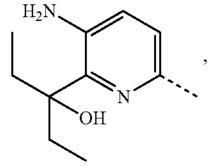
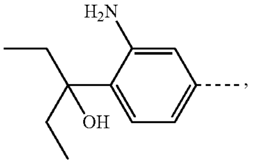
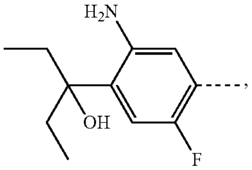
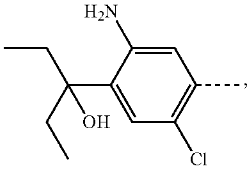
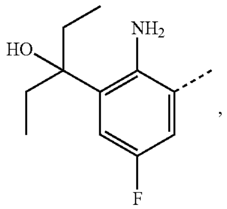
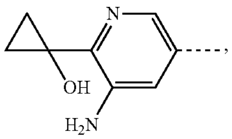
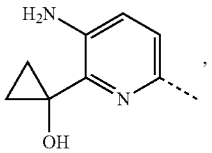
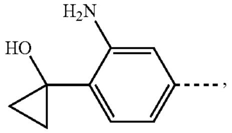
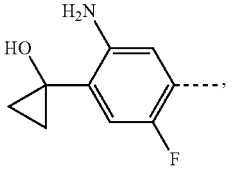
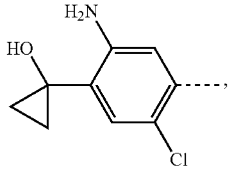
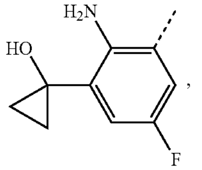
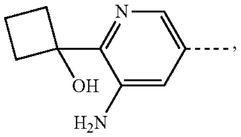
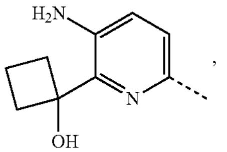
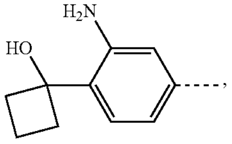
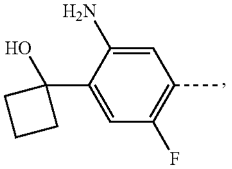
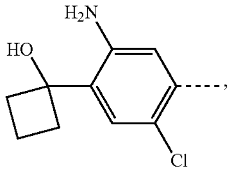
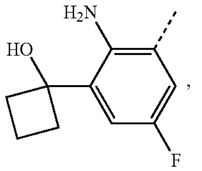
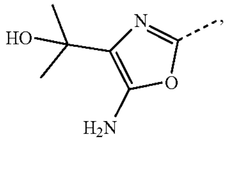
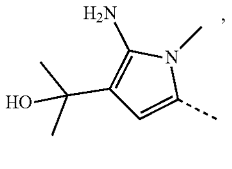
-continued
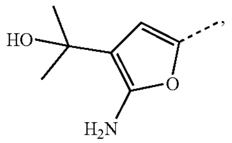
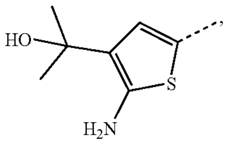
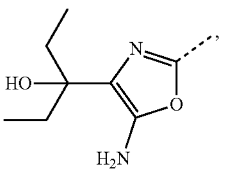
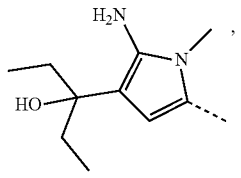
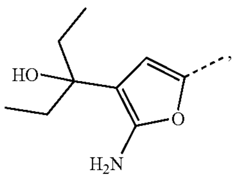
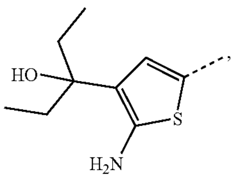
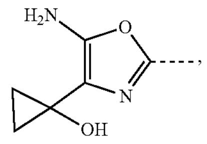
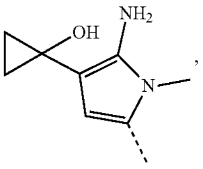
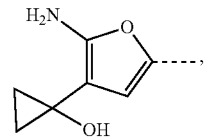
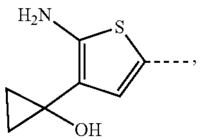
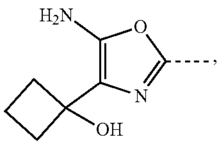
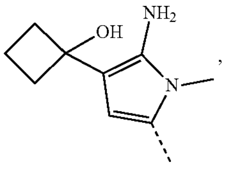
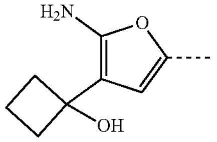
and
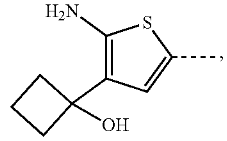
and other variables are as defined in the present disclosure.
There are also some embodiments of the present disclosure obtained by an arbitrary combination of the above variables.
In some embodiments of the present disclosure, the compound or the pharmaceutically acceptable salt thereof is selected from
(I-1)
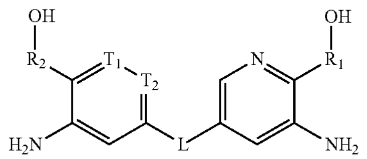
(I-2)
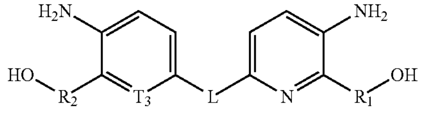

-continued (I-3)

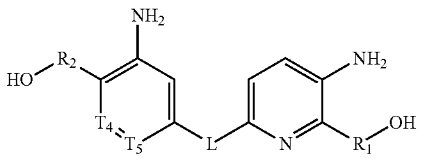

(I-4)

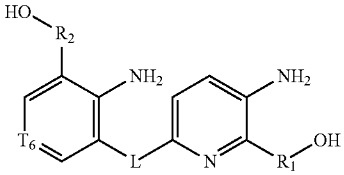

(I-5)

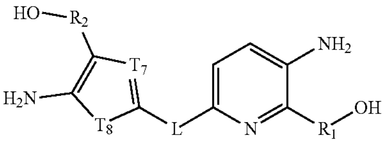

(I-6)

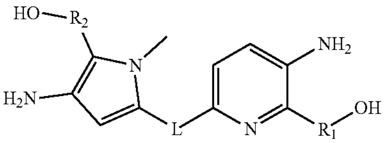

(P-1)

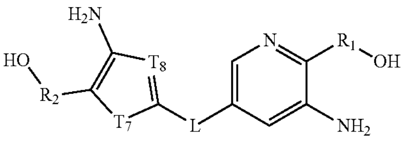

, wherein, $T_1$, $T_3$ and $T_4$ are each independently selected from N and $CR_3$;

$T_2$, $T_5$ and $T_6$ are selected from $CR_3$;

$T_7$ is selected from N and $CR_3$;

$T_8$ is selected from O and S;

$R_3$ is selected from H, F, Cl, Br, I and $CH_3$;

$R_1$, $R_2$ and L are as defined in the present disclosure.

The present disclosure also provides a compound represented by the following formula or a pharmaceutically acceptable salt thereof,

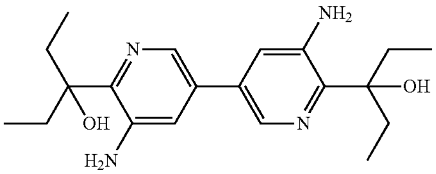

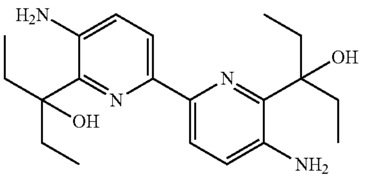

-continued

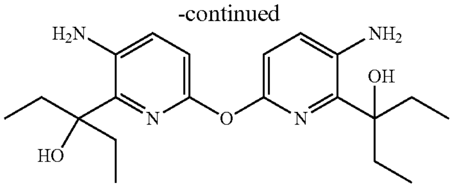

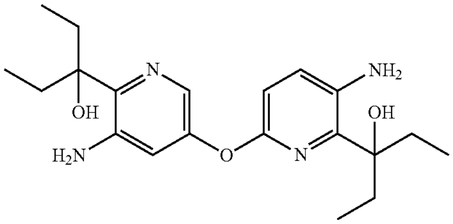

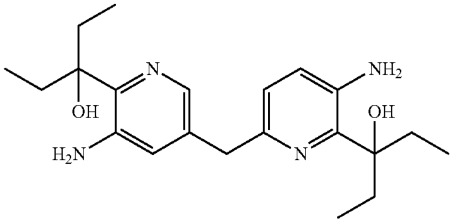

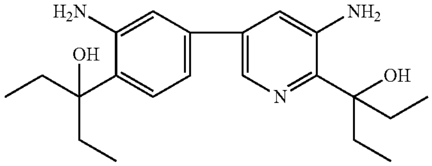

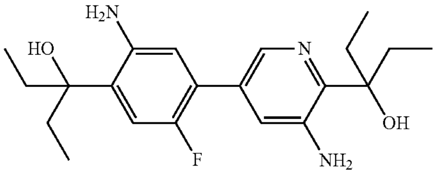

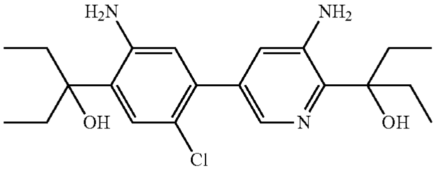

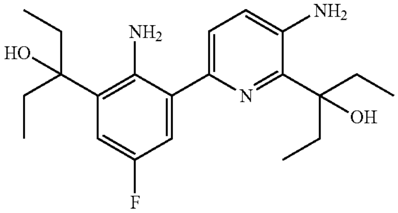

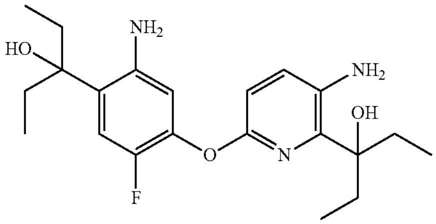

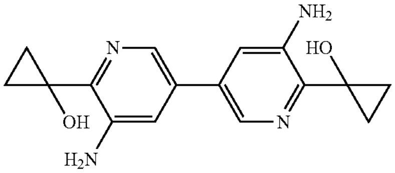

-continued
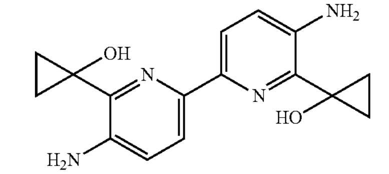
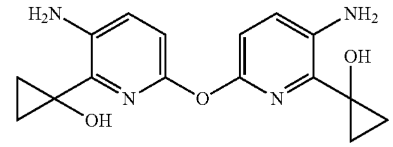
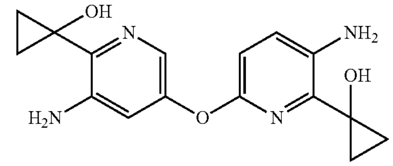
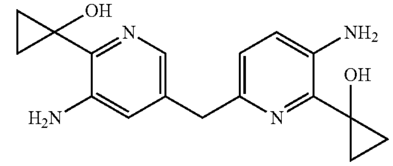
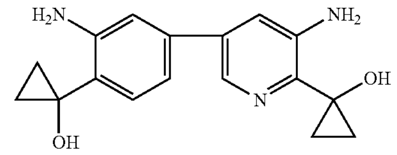
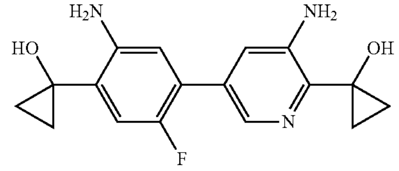
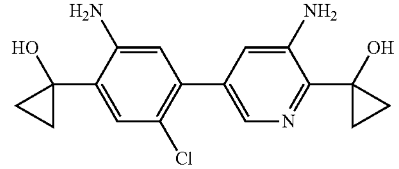
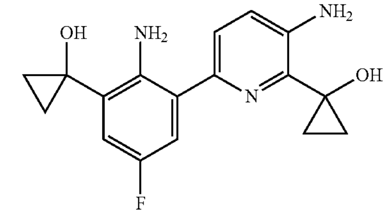
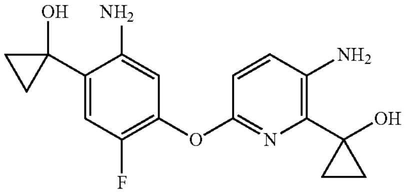
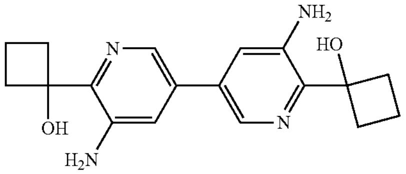
-continued
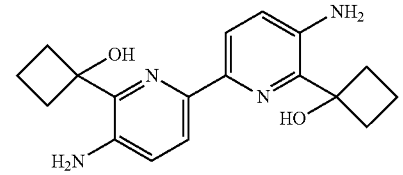
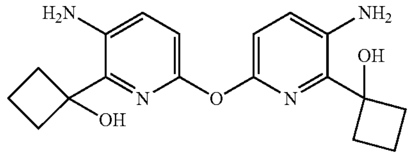
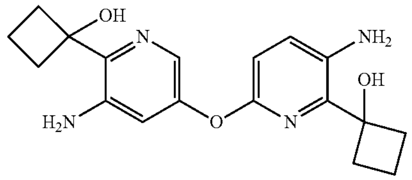
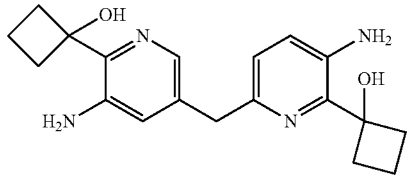
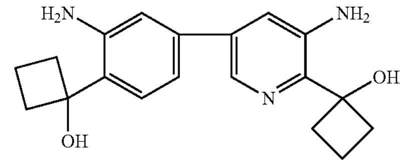
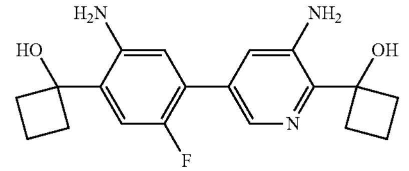
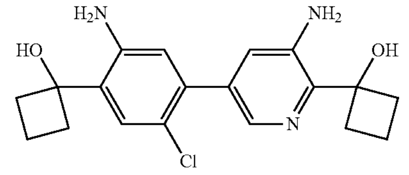
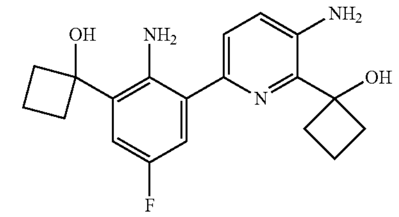
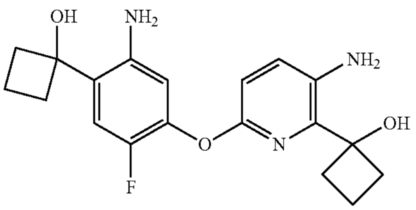

-continued
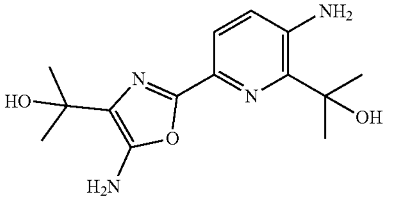
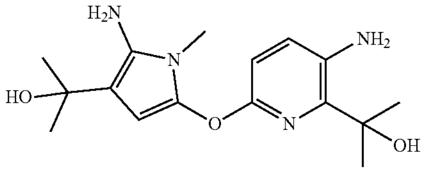
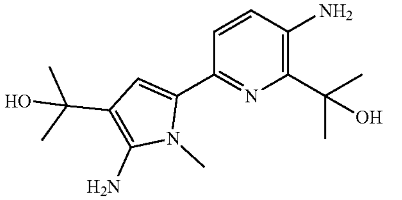
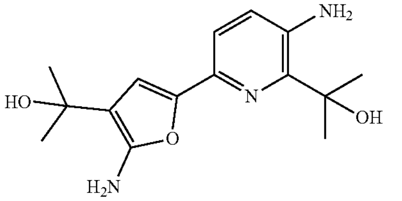
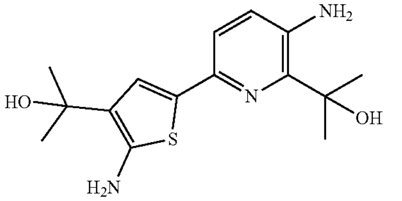
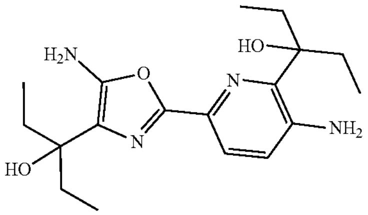
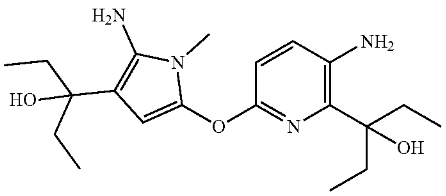
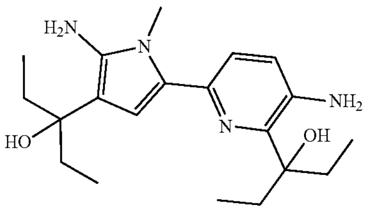
-continued
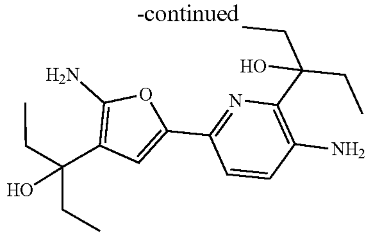
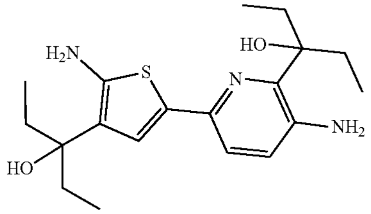
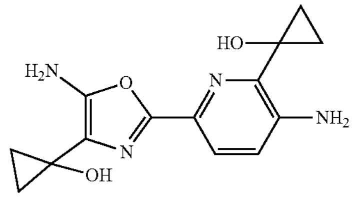
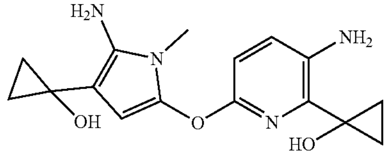
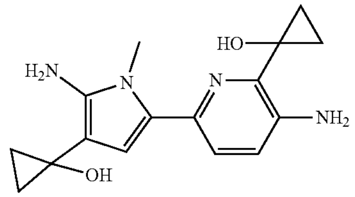
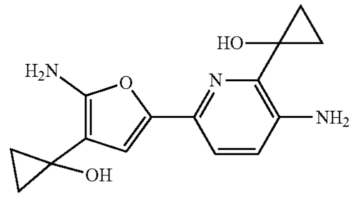
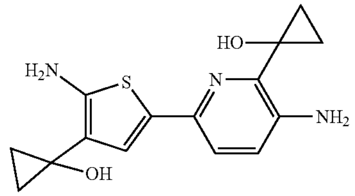
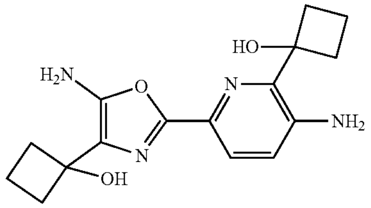
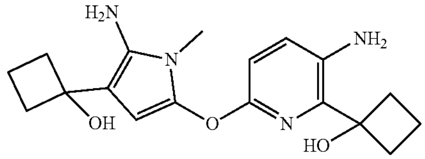

-continued

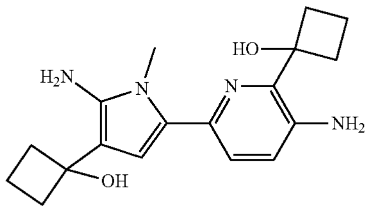

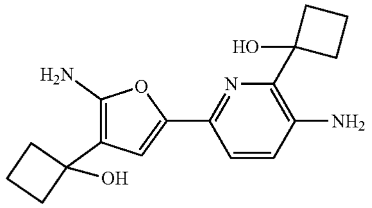

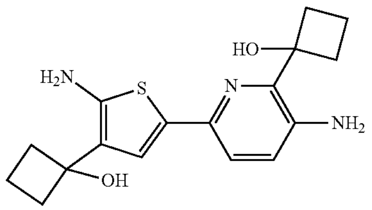

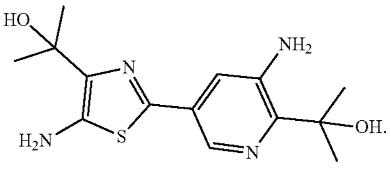

In some embodiments of the present disclosure, use of the compound or the pharmaceutically acceptable salt thereof in the manufacture of a medicament for treating diseases related to an aldehyde trapping agent.

In some embodiments of the present disclosure, use of the compound or the pharmaceutically acceptable salt thereof in the manufacture of a medicament for treating diseases related to an aldehyde-binding agent.

In some embodiments of the present disclosure, the use, wherein, the medicament for diseases related to the aldehyde trapping agent is a medicament for xerophthalmia.

The present disclosure also provides the following synthesis methods:

Route 1

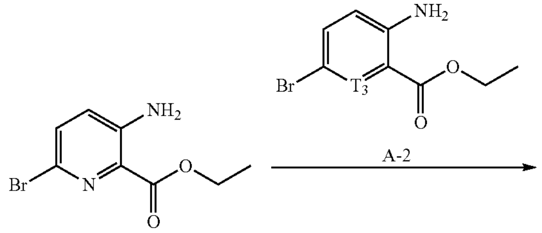

A-1

-continued

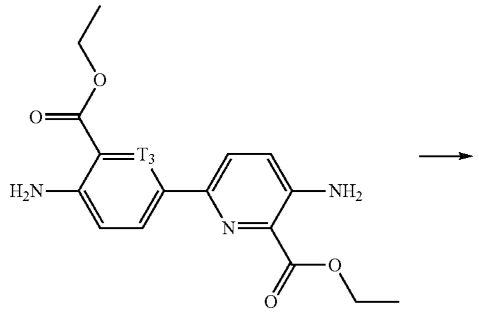

A-3

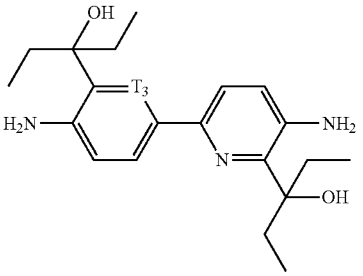

A

Route 2

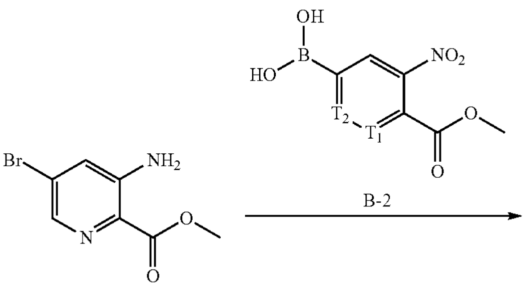

B-1

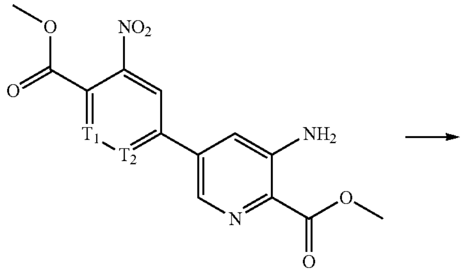

B-3

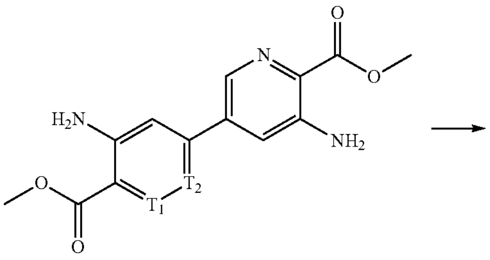

B-4

-continued

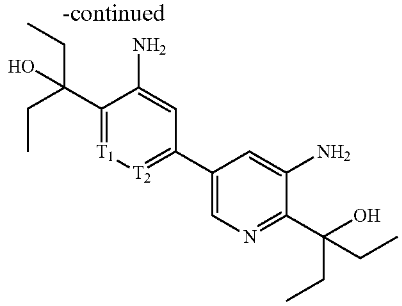

B

Route 3

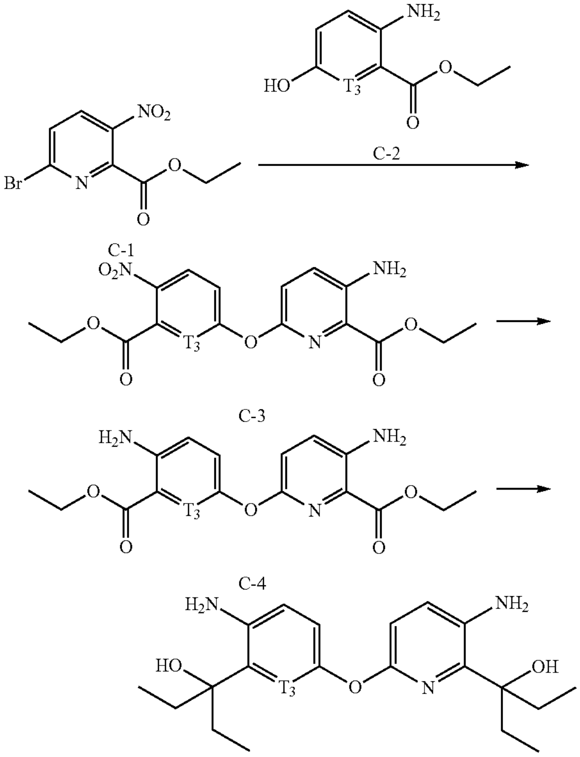

C wherein, $T_1$ and $T_3$ are each independently selected from N and $CR_3$;

$T_2$ is selected from $CR_3$;

$R_3$ is selected from H, F, Cl, Br, I and $CH_3$.

Definitions and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt may be obtained by bringing the neutral form of the compound into contact with a sufficient amount of base in a pure solution or a suitable inert solvent. The pharmaceutically acceptable base addition salt includes a salt of sodium, potassium, calcium, ammonium, organic ammonia or magnesium, or similar salts. When the compound of the present disclosure contains a relatively basic functional group, an acid addition salt may be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

In addition to salt forms, the compounds provided in the present disclosure also exist in prodrug forms. The prodrugs of the compounds described herein easily undergo chemical changes under physiological conditions to be converted into the compounds of the present disclosure. Furthermore, the prodrugs may be converted to the compounds of the present disclosure by chemical or biochemical methods in an in vivo environment.

Some compounds of the present disclosure may exist in a non-solvated or solvated form, including a hydrate form. Generally speaking, the solvated form is equivalent to the non-solvated form, and both are included in the scope of the present disclosure.

Optically active (R)- and (S)-isomers, as well as D and L isomers can be prepared by chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to obtain the pure enantiomer. In addition, the enantiomer and the diastereoisomer are generally isolated through chromatography which uses a chiral stationary phase and optionally combines with a chemical derivative method (such as carbamate generated from amine).

The compound of the present disclosure may contain an unnatural proportion of atomic isotope at one or more than one atom(s) that constitute the compound. For example, the compound can be labeled with a radioactive isotope, such as tritium ($^{3}H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs and the like. All isotopic variations of the compound of the present disclosure, whether radioactive or not, are encompassed within the scope of the present disclosure.

The term “optional” or “optionally” means that the subsequent event or condition may occur but not requisite, that the term includes the instance in which the event or condition occurs and the instance in which the event or condition does not occur.

The term “substituted” means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are replaced. Oxo substituents are not present on aromatic moieties.

The term “optionally substituted” means an atom can be substituted with a substituent or not, unless otherwise specified, the type and number of the substituent may be arbitrary as long as is chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only if the combination results in a stable compound.

When the number of a linking group is 0, such as $-(CRR)_0-$, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring. When the enumerative linking group does not indicate the direction for linking, the direction for linking is arbitrary, for example, the linking group L contained in

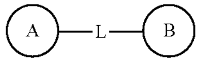

is -M-W—, then -M-W— can link ring A and ring B to form

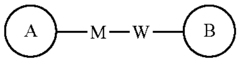

in the direction same as left-to-right reading order, and form

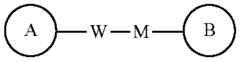

in the direction contrary to left-to-right reading order. A combination of the linking groups, substituents and/or variables thereof is allowed only when such combination can result in a stable compound.

Unless otherwise specified, the term “$C_{1-6}$ alkyl” refers to a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl, etc.; it can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, and t-butyl), pentyl (including n-pentyl, isopentyl and neopentyl), hexyl and the like.

Unless otherwise specified, “$C_{3-5}$ cycloalkyl” refers to a saturated cyclic hydrocarbon group composing of 3 to 5 carbon atoms, which is a monocyclic ring system, and the $C_{3-5}$ cycloalkyl includes $C_{3-4}$ and $C_{4-5}$ cycloalkyl and the like; it can be monovalent, divalent or multivalent. Examples of $C_{3-5}$ cycloalkyl include, but are not limited to, cyclopropyl, cyclobutyl, cyclopentyl and the like.

Unless otherwise specified, the terms “5-membered heteroaromatic ring” and “5-membered heteroaryl” in the present disclosure may be used interchangeably, and the term “5-membered heteroaryl” refers to a monocyclic group consisting of 5 ring atoms with conjugated π electronic system, of which 1, 2, 3 or 4 ring atoms are heteroatoms independently selected from O, S and N, and the rest are carbon atoms. Wherein the nitrogen atom is optionally quaternized, and the nitrogen and sulfur heteroatoms are optionally oxidized (i.e., NO and $S(O)_p$, where p is 1 or 2). The 5-membered heteroaryl may be attached to the rest of the molecule through a heteroatom or a carbon atom. Examples of the 5-membered heteroaryl include, but are not limited to, pyrrolyl (including N-pyrrolyl, 2-pyrrolyl and 3-pyrrolyl and the like), pyrazolyl (including 2-pyrazolyl and 3-pyrazolyl and the like), imidazolyl (including N-imidazolyl, 2-imidazolyl, 4-imidazolyl and 5-imidazolyl and the like), oxazolyl (including 2-oxazolyl, 4-oxazolyl and 5-oxazolyl and the like), triazolyl (1H-1,2,3-triazolyl, 2H-1,2,3-triazolyl, 1H-1,2,4-triazolyl and 4H-1,2,4-triazolyl and the like), tetrazolyl, isoxazolyl (3-isoxazolyl, 4-isoxazolyl and 5-isoxazolyl and the like), thiazolyl (including 2-thiazolyl, 4-thiazolyl and 5-thiazolyl and the like), furanyl (including 2-furanyl and 3-furanyl and the like), and thienyl (including 2-thienyl and 3-thienyl and the like).

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$ and the like; similarly, n-membered to n+m-membered means that the number of atoms on the ring is from n to n+m, for example, 3-12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3-12-membered ring includes 3-6-membered ring, 3-9-membered ring, 5-6-membered ring, 5-7-membered ring, 6-7-membered ring, 6-8-membered ring, and 6-10-membered ring and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The solvent used in the present disclosure is commercially available. The following abbreviations are used in the present disclosure: aq. stands for aqueous solution; eq. stands for equivalent, equivalence; DCM stands for dichloromethane; PE stands for petroleum ether; DMSO stands for dimethyl sulfoxide; EtOAc stands for ethyl acetate; EtOH stands for ethanol; MeOH represents methanol; CBz stands for benzyloxycarbonyl, which is an amine protecting group; HOAc stands for acetic acid; r.t. stands for room temperature; O/N stands for overnight; THE stands for tetrahydrofuran.

The compounds of the present disclosure are named according to the conventional naming principles in the art or by ChemDraw® software, and the commercially available compounds use the supplier catalog names.

Technical Effect

The compound of the present disclosure has good aldehyde complexing ability, which is helpful to relieve eye inflammation and achieve the purpose of treating xerophthalmia.

BRIEF DESCRIPTION OF THE DRAWINGS

The FIGURE is the test result of in vitro aldehyde-trapping ability of the compound of the present disclosure.

DETAILED DESCRIPTION OF THE PREFERRED EMBODIMENT

The present disclosure is described in detail by the embodiments below, but it does not mean that there are any adverse restrictions on the present disclosure. The present disclosure has been described in detail herein, and its specific embodiments have also been disclosed, for one skilled in the art, it is obvious to make various modifications and improvements to the embodiments of the present disclosure without departing from the spirit and scope of the present disclosure.

Embodiment 1

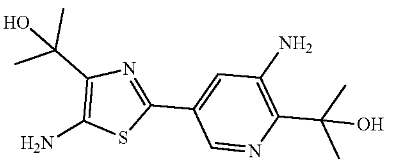

1

Synthetic Route:

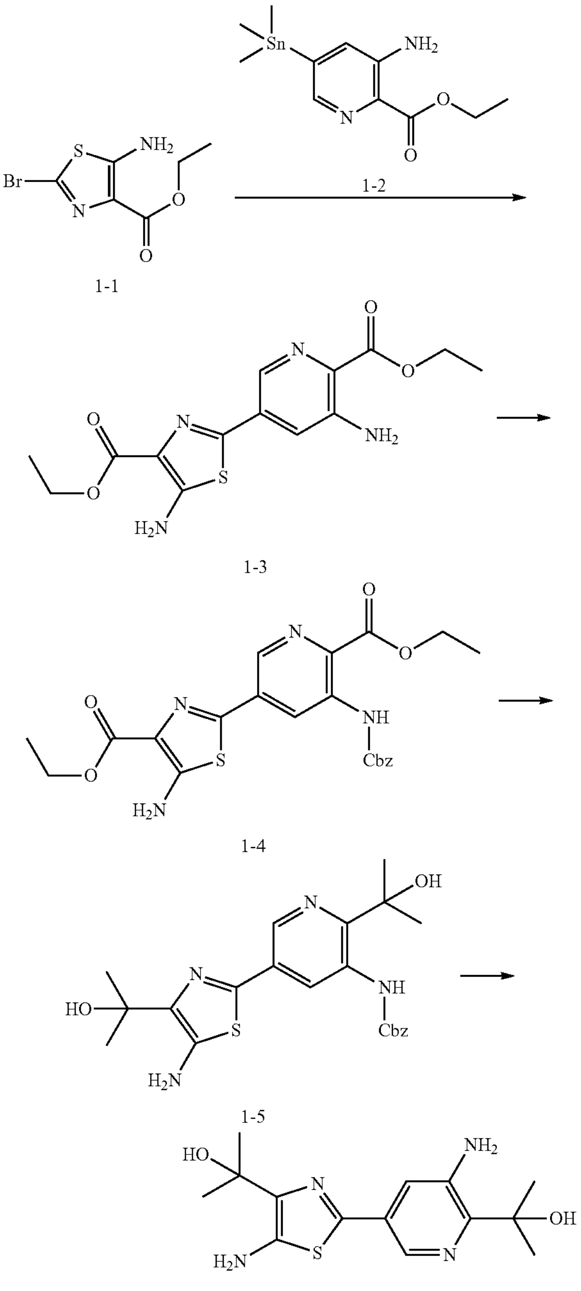

1-1

1-2

1-3

1-4

1-5

1

Step 1: Preparation of Compound 1-3

Compound 1-1 (1 g, 3.98 mmol, 1 eq) and compound 1-2 (1.44 g, 4.38 mmol, 1.1 eq) were dissolved in toluene (20 mL), and tetrakistriphenylphosphine (460 mg, 398.08 μmol, 0.1 eq) was added to the reaction solution. The reactor was replaced three times with nitrogen, and the mixture was heated to 130° C. and stirred for 2 hours. The mixture was cooled to room temperature, filtered, and the filter cake was rinsed with 5 mL of toluene. The filter cake was collected and dried to obtain compound 1-3 without further purification.

$^1$H NMR (400 MHz, DMSO-$d_6$) δ 8.18 (d, J=2.0 Hz, 1H), 7.74 (s, 2H), 7.57 (d, J=2.0 Hz, 1H), 6.84 (s, 2H), 4.30 (dq, J=2.5, 7.0 Hz, 4H), 1.32 (dt, J=4.8, 7.2 Hz, 6H).

Step 2: Preparation of Compound 1-4

Compound 1-3 (500 mg, 1.49 mmol, 1 eq) and triethylamine (472.55 mg, 4.67 mmol, 0.65 mL, 3.14 eq) were dissolved in tetrahydrofuran (10 mL), cooled to 0° C., and benzyl chloroformate (600.00 mg, 3.52 mmol, 500.00 μL, 2.37 eq) was added dropwise thereto. After the addition was completed, the reaction was stirred at 0 to 25° C. for 12 hours. After the reaction was completed, the mixture was added with water (20 mL) to quench the reaction, extracted with ethyl acetate (30 mL*3), and the organic phases were combined, dried over anhydrous sodium sulfate, filtered and concentrated. The residue was purified by column chromatography (petroleum ether:ethyl acetate=2:1) to obtain compound 1-4.

$^1$H NMR (400 MHz, DMSO-$d_6$) δ 8.32 (d, J=2.0 Hz, 1H), 7.78 (d, J=2.0 Hz, 1H), 7.53-7.37 (m, 5H), 6.89 (s, 2H), 5.32 (s, 2H), 4.44-4.27 (m, 4H), 1.34 (dt, J=5.5, 7.0 Hz, 6H).

Step 3: Preparation of Compound 1-5

Compound 1-4 (300 mg, 637.62 μmol, 1 eq) was dissolved in tetrahydrofuran (20 mL), cooled to 0° C., and methylmagnesium bromide (3 M, 6.38 mL, 30 eq) was added dropwise thereto. After the addition was completed, the reaction was stirred at 0° C. for 2 hours. After the reaction was completed, the mixture was added with water (20 mL) to quench, extracted with ethyl acetate (30 mL*3), and the organic phases were combined and concentrated under reduced pressure. The residue was purified by column chromatography (petroleum ether:ethyl acetate=2:1) to obtain compound 1-5.

$^1$H NMR (400 MHz, $CDCl_3$) δ 9.30-9.17 (m, 1H), 8.26 (s, 1H), 7.43-7.28 (m, 7H), 5.26-5.12 (m, 2H), 1.72 (s, 6H), 1.69 (s, 6H).

Step 4: Preparation of Compound 1

Compound 1-5 (50 mg, 112.99 μmol, 1 eq) and Pd/C (100 mg, 10% content) were added to methanol (10 mL), and the reaction was stirred at 25° C. for 3 hours under the protection of hydrogen sphere (15 psi). After the reaction was completed, the reaction solution was filtered and concentrated under reduced pressure. The residue was purified by column chromatography (petroleum ether:ethyl acetate=1:1) to obtain compound 1.

$^1$H NMR (400 MHz, MeOD) δ 8.09 (d, J=2.0 Hz, 1H), 7.39 (d, J=2.0 Hz, 1H), 1.63 (s, 12H).

Experimental Embodiment 1: Experiment of Aldehyde-Trapping Ability in Vitro

1. Experimental Objective and Process

Objective: xerophthalmia is caused by inflammations inside the eye, and these inflammations would produce some aldehydes in vivo. If these aldehydes are not eliminated in time, the symptoms of inflammations would be accelerated and worsen the xerophthalmia. In this experiment, by simulating the in vivo environment, a relatively preferred compound was selected according to the complexing ability of the drug and the aldehyde in vivo.

Process: sulfobutyl-B-cyclodextrin (310 mg) was dissolved in phosphate buffer (1.25 mL) to prepare a solution.

Nonanal (5.0 mg, 32 μmol, 1.0 eq) and glyceryl trioleate (300 mg) were added into a reaction flask at room temperature. After the above prepared solution was added thereto, linoleic acid (300 mg) was then added thereto, and finally a dimethyl sulfoxide (0.15 mL) solution containing the compound of the present disclosure (32 μmol, 1.0 eq) was added thereto. The reaction solution was reacted at 20 to 23° C.

After stirring and reacting for 10 minutes, 100 minutes, 200 minutes, and 300 minutes, respectively, the reaction solution was allowed to stand for 2 minutes, layered and then sampled for high performance liquid detection.

Sampling method: 25 μL of the upper emulsion layer and 50 μL of the lower aqueous phase were sampled with a pipette, and diluted with 1 mL of methanol.

2. Experimental Results

Nonanal has weak ultraviolet absorption at a wavelength of 254 nm, and has little influence on the content of complexation product as a whole. Therefore, the percentage content of the complexed compound at 254 nm in high performance liquid phase was compared to observe the ability of the compound to trap and complex aldehyde. See FIG. 1 and Table 3:

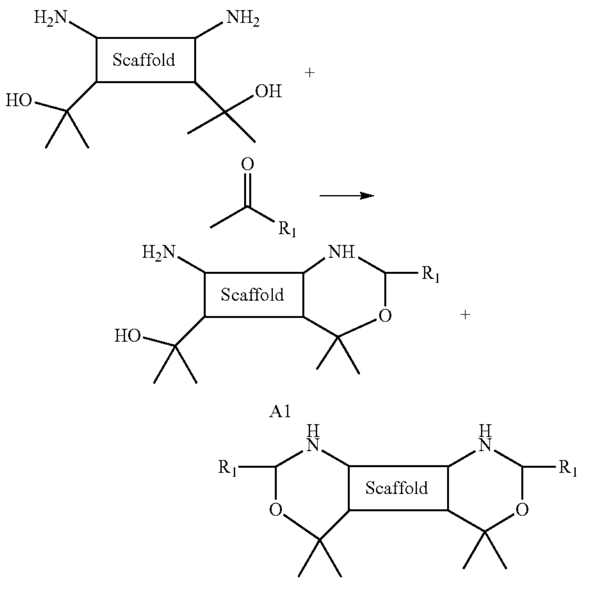

A1

A2

The HPLC analysis method is shown in Table 1 below, which is XBRIGE 2.5 μm, 3.0*100 mm 5-95CD_XBEH_12 min_0.8.lcm

TABLE 1

| | | | |
|---|---|---|---|
| Chromatographic column | XBridge BEH C18 3.0*100 mm, 2.5 μm | | |
| Detection wavelength | 220, 254 nm | | |
| Column temperature | 40° C. | | |
| Flow rate | 0.8 mL/min | | |
| Injection volume | 1 μL | | |
| Mobile phase | A: 0.02% aqueous ammonia solution<br>B: acetonitrile | | |
| Gradient elution | Time (minutes) | A % | B % |
| | 0.01 | 95 | 5 |
| | 6.00 | 15 | 85 |
| | 9.00 | 5 | 95 |
| | 12.00 | 5 | 95 |

The specific HPLC data of the percentage content of the complex product of the compound of the present disclosure are as shown in Table 2 below:

TABLE 2

| | Time (minutes) | | | |
|---|---|---|---|---|
| Compound | 10 | 100 | 200 | 300 |
| 1 | 1.095 | 4.751 | 8.764 | 12.496 |

TABLE 3

Statistics of test results of aldehyde-trapping ability of the compound

| Compound | Linear equation | Slope | Regression coefficient $R^2$ | Area under the curve AUC (min. conversion rate) |
|---|---|---|---|---|
| Compound 1 | y = 0.0394x + 0.7705 | 0.0394 | $R^2$ = 0.9996 | 1874 |

Conclusion: The compound of the present disclosure has remarkable ability and speed to complex aldehyde.

What is claimed is:

1. A compound represented by formula (I) or a pharmaceutically acceptable salt thereof,

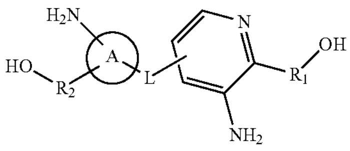

(I)

wherein,

L is selected from —O— and —$(CR_4R_5)_n$—;

$R_1$ is selected from —$C_{1-6}$ alkyl- and —$C_{3-5}$ cycloalkyl-, and the —$C_{1-6}$ alkyl- and —$C_{3-5}$ cycloalkyl- are optionally substituted by 1, 2 or 3 $R_a$;

ring A is selected from phenyl, pyridyl and 5-membered heteroaryl, and the phenyl, pyridyl and 5-membered heteroaryl are optionally substituted by 1, 2 or 3 $R_3$;

and when ring A is selected from phenyl and pyridyl, $R_2$ is selected from —$C_{5-6}$ alkyl- and —$C_{3-5}$ cycloalkyl-, and the —$C_{5-6}$ alkyl- and —$C_{3-5}$ cycloalkyl- are optionally substituted by 1, 2 or 3 $R_b$;

when ring A is selected from 5-membered heteroaryl, $R_2$ is selected from —$C_{1-6}$ alkyl- and —$C_{3-5}$ cycloalkyl-, and the —$C_{1-6}$ alkyl- and —$C_{3-5}$ cycloalkyl- are optionally substituted by 1, 2 or 3 $R_c$;

$R_3$ is selected from H, F, Cl, Br, I and $CH_3$;

$R_4$ and $R_5$ are each independently selected from H and $CH_3$;

n is selected from 0, 1 and 2;

$R_a$, $R_b$ and $R_c$ are each independently selected from F, Cl, Br and I;

the "5-membered heteroaryl" comprises 1, 2, 3 or 4 heteroatoms or heteroatom groups independently selected from —O—, —NH—, —S— and N, respectively.

2. The compound or the pharmaceutically acceptable salt thereof according to claim 1, wherein $R_1$ is selected from $CH_2$, $C(CH_3)_2$, $C(CH_2CH_3)_2$, cyclopropyl and cyclobutyl, and the $CH_2$, $C(CH_3)_2$, $C(CH_2CH_3)_2$, cyclopropyl and cyclobutyl are optionally substituted by 1, 2 or 3 $R_a$;

or, L is selected from a single bond, —O—, $CH_2$ and —$CH_2CH_2$—.

3. The compound or the pharmaceutically acceptable salt thereof according to claim 2, wherein $R_1$ is selected from $C(CH_3)_2$, $C(CH_2CH_3)_2$, cyclopropyl and cyclobutyl.

4. The compound or the pharmaceutically acceptable salt thereof according to claim 1, wherein when ring A is selected from phenyl and pyridyl, $R_2$ is selected from $C(CH_2CH_3)_2$, cyclopropyl and cyclobutyl;

when ring A is selected from 5-membered heteroaryl, $R_2$ is selected from $C(CH_3)_2$, $C(CH_2CH_3)_2$, cyclopropyl and cyclobutyl.

5. The compound or the pharmaceutically acceptable salt thereof according to claim 1, wherein ring A is selected from phenyl, pyridyl, pyrrolyl, furyl, thienyl, oxazolyl and thiazolyl, and the phenyl, pyridyl, pyrrolyl, furyl, thienyl, oxazolyl and thiazolyl are optionally substituted by 1, 2 or 3 $R_3$.

6. The compound or the pharmaceutically acceptable salt thereof according to claim 5, wherein ring A is selected from

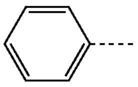, 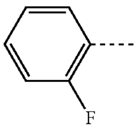, 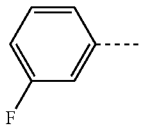, 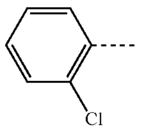, 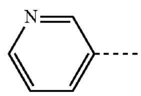, 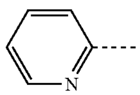, 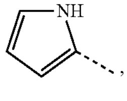, 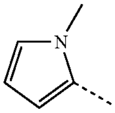, 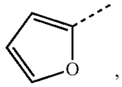, 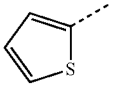, -continued
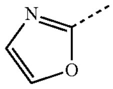
and
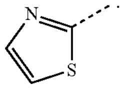
7. The compound or the pharmaceutically acceptable salt thereof according to claim 1, wherein the structural unit
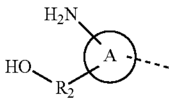
is selected from
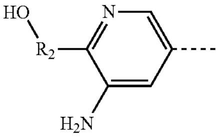
,
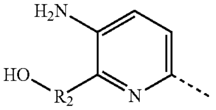
,
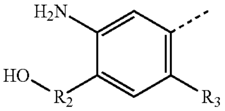
,
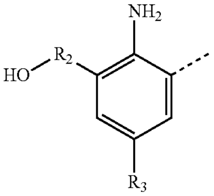
,
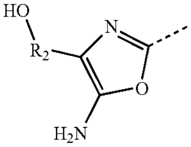
,
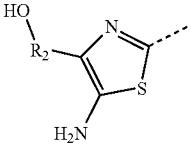
,
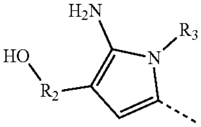
,
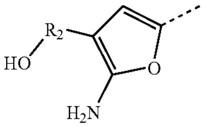
and
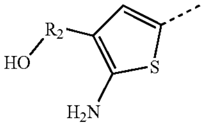
.
8. The compound or the pharmaceutically acceptable salt thereof according to claim 7, wherein the structural unit
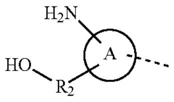
is selected from
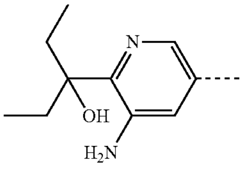
,
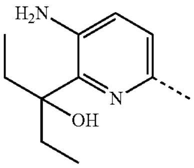
,
-continued
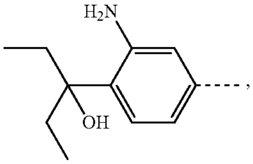
,
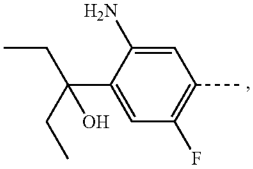
,
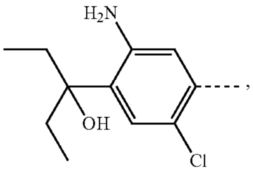
,
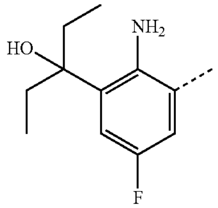
,
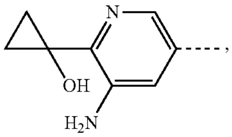
,
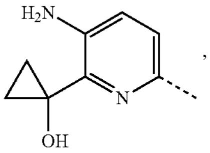
,
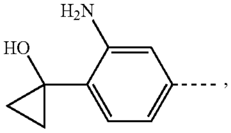
,
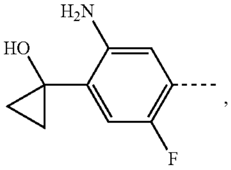
,
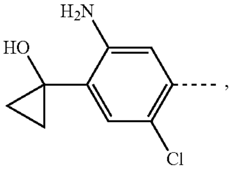
,
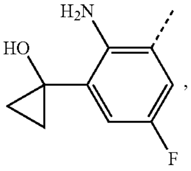
,
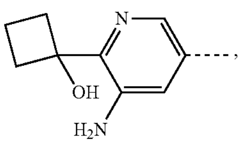
,
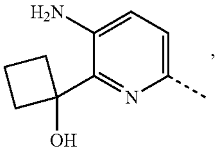
,
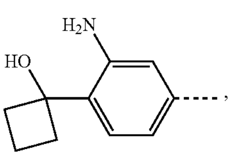
,
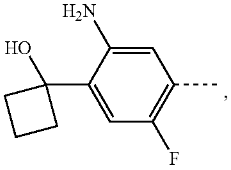
,
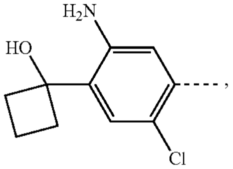
,
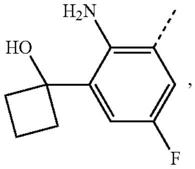
,
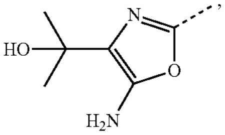
,
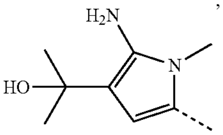
,
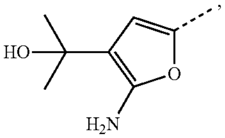
,
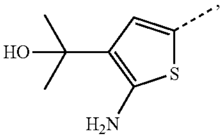
, -continued

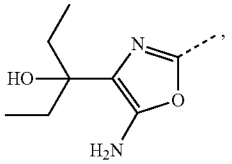,
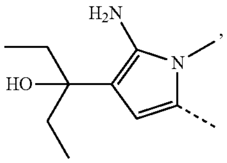,
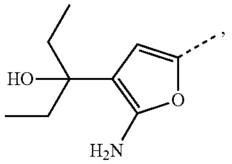,
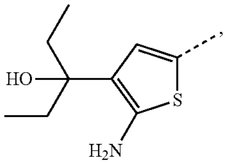,
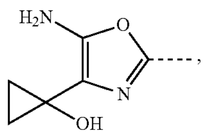,
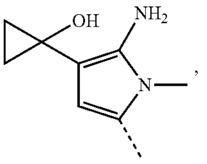,
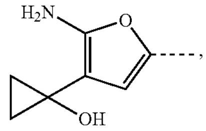,
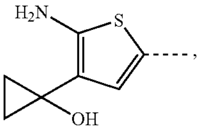,
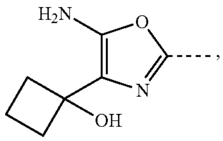,
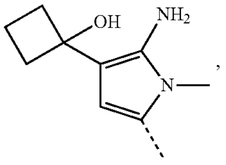,
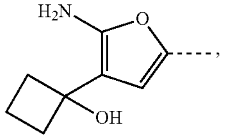,
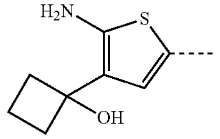 and
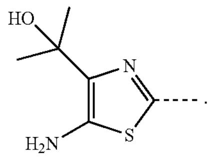.

9. The compound or the pharmaceutically acceptable salt thereof according to claim 1, selecting from, (I-1)

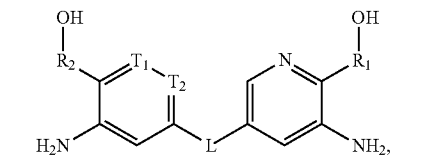

(I-2)

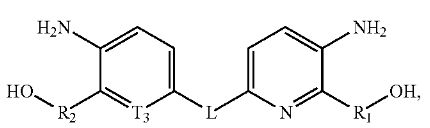

(I-3)

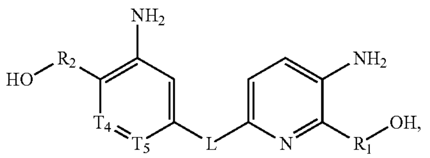

-continued (I-4)

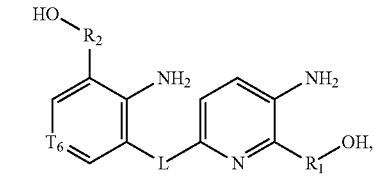

(I-5)

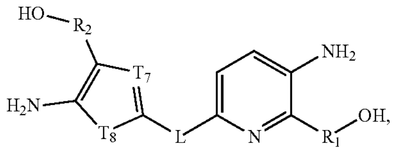

(I-6)

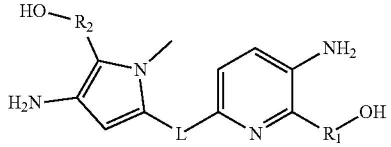 and (P-1)

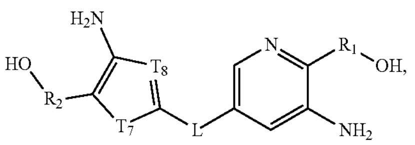

wherein, $T_1$, $T_3$ and $T_4$ are each independently selected from N and $CR_3$;

$T_2$, $T_5$ and $T_6$ are selected from $CR_3$;

$T_7$ is selected from N and $CR_3$;

$T_8$ is selected from O and S;

$R_3$ is selected from H, F, Cl, Br, I and $CH_3$;

$R_1$, $R_2$ and L are as defined in claim 1.

10. A compound represented by the following formula or a pharmaceutically acceptable salt thereof, wherein the compound is selected from any one of the following compounds:

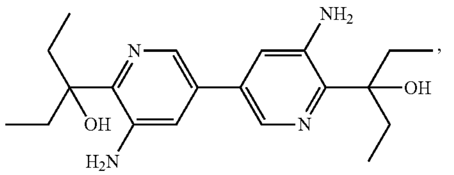

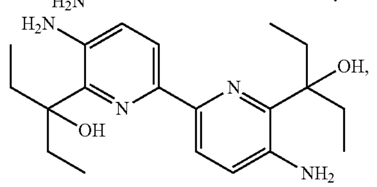

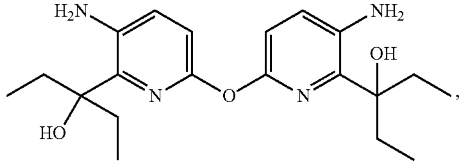

-continued
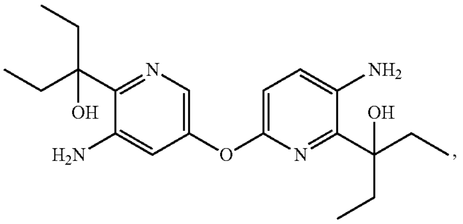
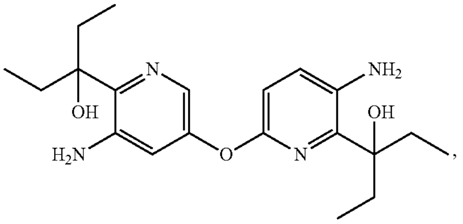
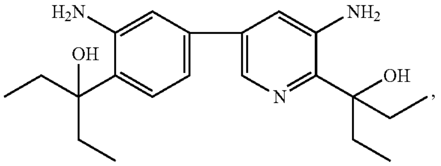
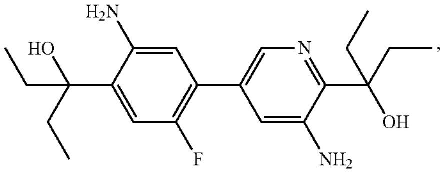
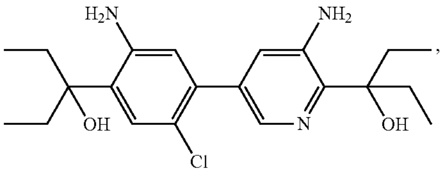
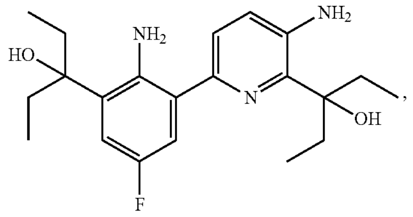
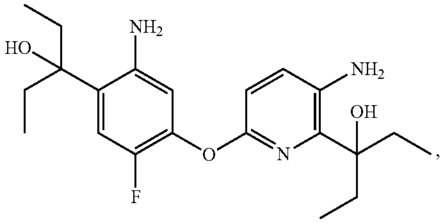
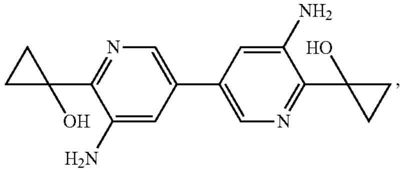
-continued
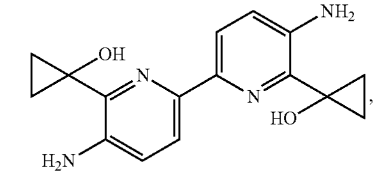
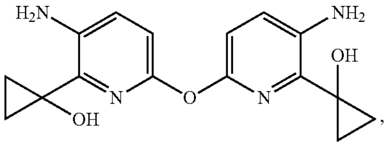
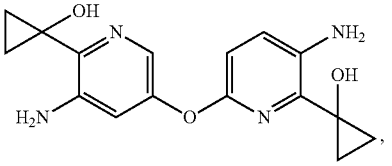
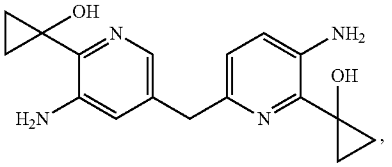
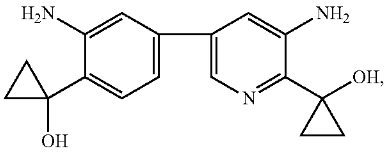
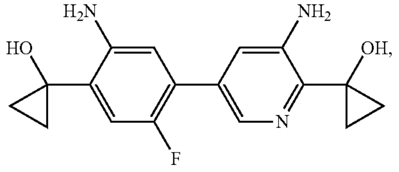
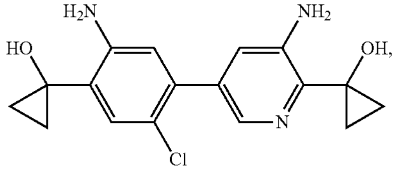
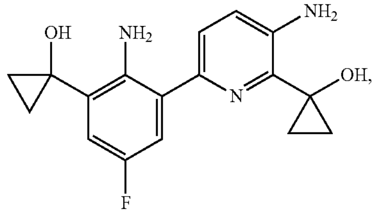
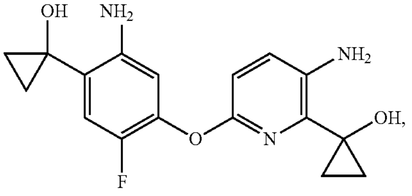
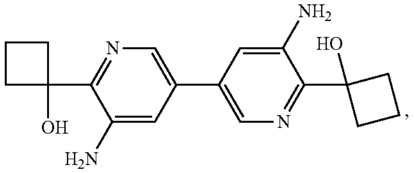

-continued
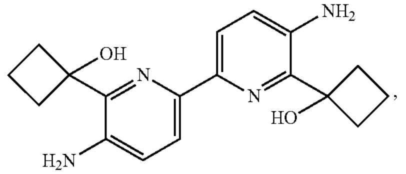
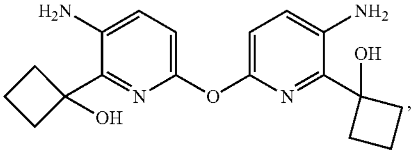
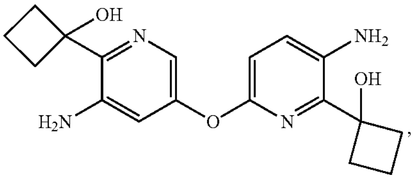
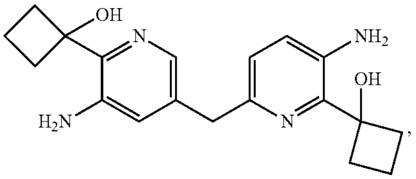
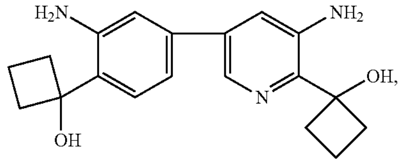
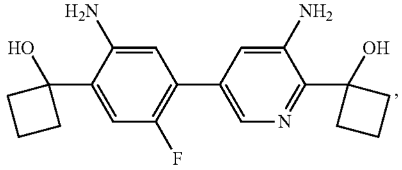
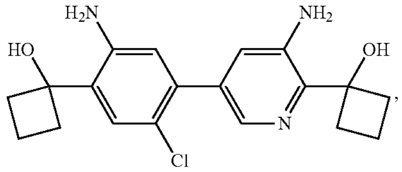
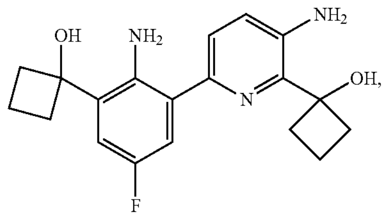
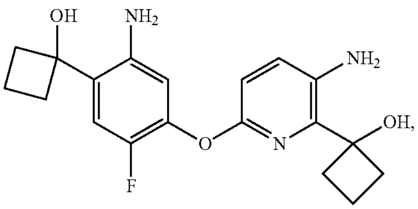
-continued
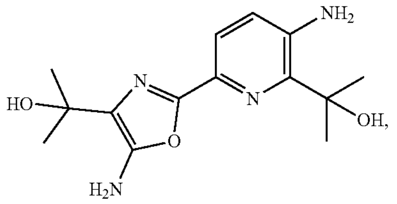
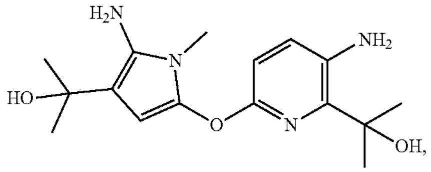
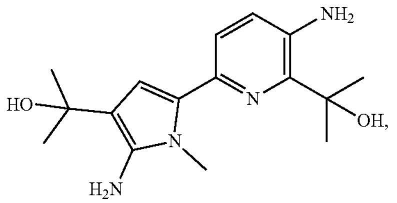
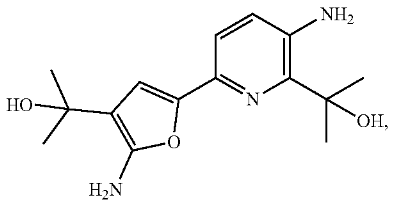
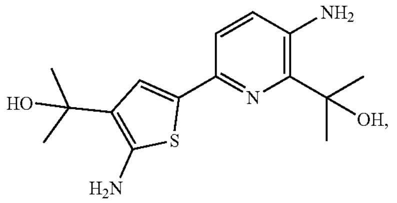
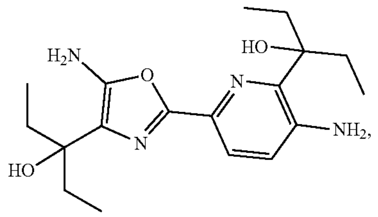
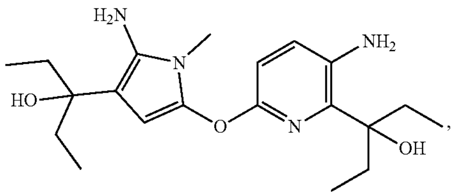
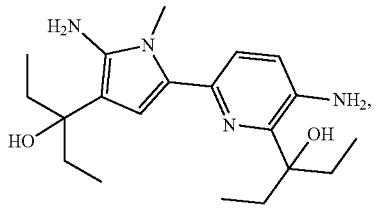

-continued

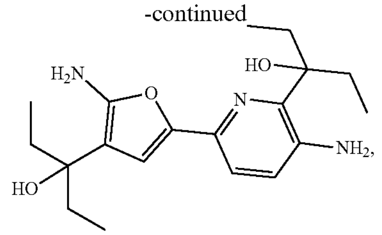

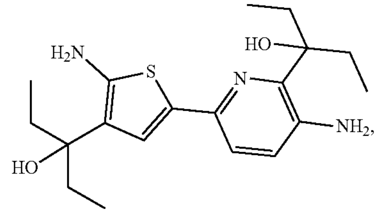

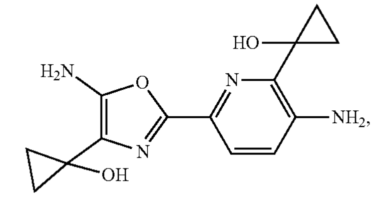

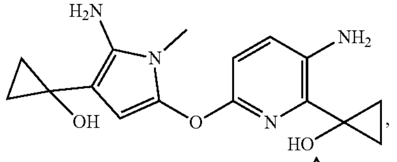

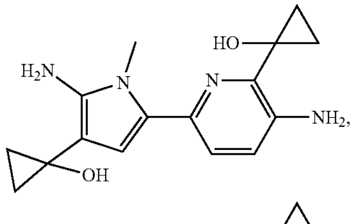

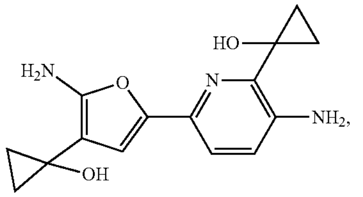

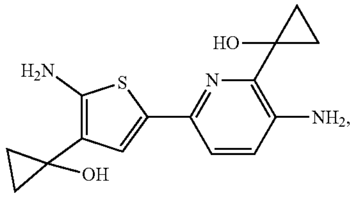

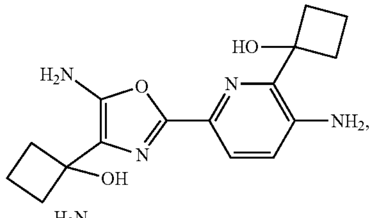

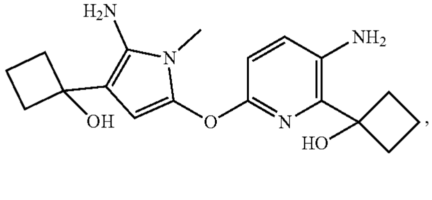

-continued

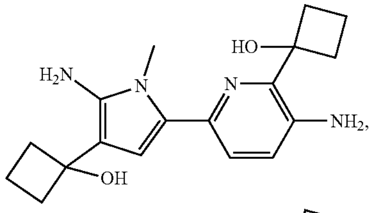

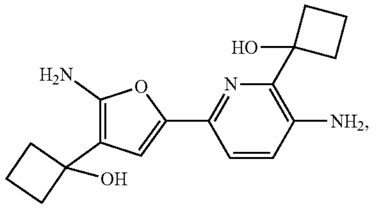

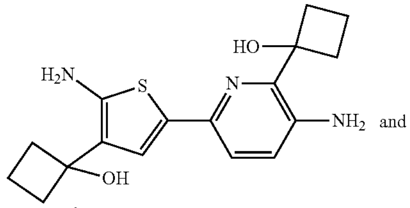

and

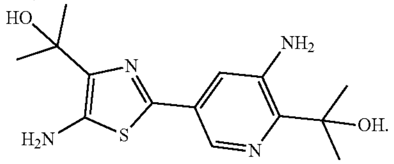

11. A method for treating diseases related to an aldehyde trapping agent in a subject in need thereof, comprising: administering an effective amount of the compound or the pharmaceutically acceptable salt thereof according to claim 1 to the subject, wherein, the diseases related to the aldehyde trapping agent is xerophthalmia.

12. A method for treating diseases related to an aldehyde trapping agent in a subject in need thereof, comprising: administering an effective amount of the compound or the pharmaceutically acceptable salt thereof according to claim 10 to the subject, wherein, the diseases related to the aldehyde trapping agent is xerophthalmia.

13. The compound or the pharmaceutically acceptable salt thereof according to claim 1, wherein ring A is selected from 5-membered heteroaryl and 5-membered heteroaryl are optionally substituted by 1, 2 or 3 $R_3$, $R_2$ is selected from —$C_{1-6}$ alkyl- and —$C_{3-5}$ cycloalkyl-, and the —$C_{1-6}$ alkyl- and —$C_{3-5}$ cycloalkyl- are optionally substituted by 1, 2 or 3 $R_c$.

14. The compound or the pharmaceutically acceptable salt thereof according to claim 1, wherein ring A is selected from pyrrolyl, furyl, thienyl, oxazolyl and thiazolyl, and the pyrrolyl, furyl, thienyl, oxazolyl and thiazolyl are optionally substituted by 1, 2 or 3 $R_3$.

15. The compound or the pharmaceutically acceptable salt thereof according to claim 1, wherein ring A is selected from

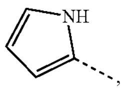

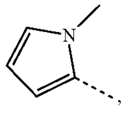

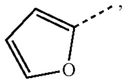

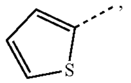

-continued

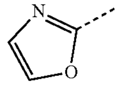 and 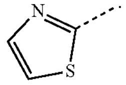

16. The compound or the pharmaceutically acceptable salt thereof according to claim 1, wherein the structural unit

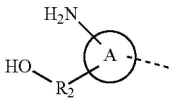

is selected from

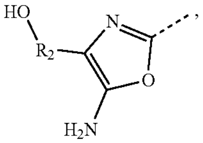
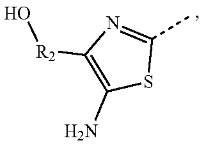
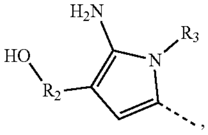
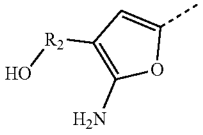
and
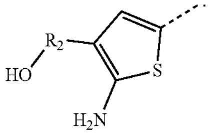

17. The compound or the pharmaceutically acceptable salt thereof according to claim 1, wherein the structural unit

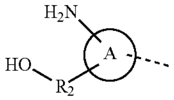

is selected from

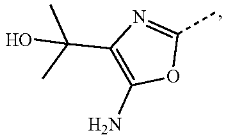
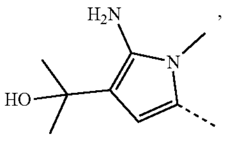
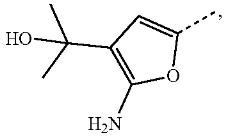
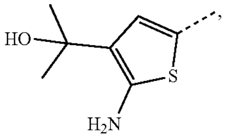

-continued

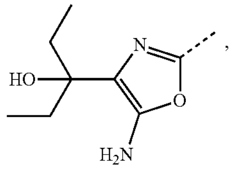
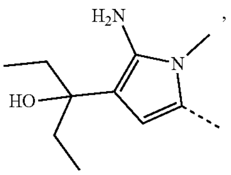
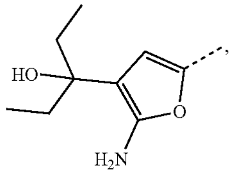
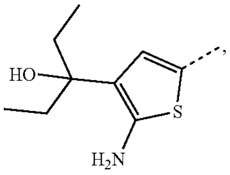
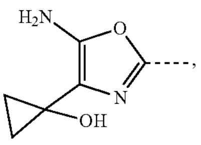
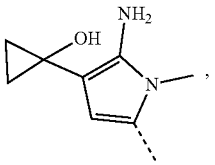
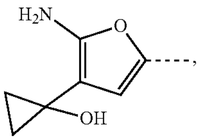
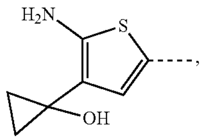
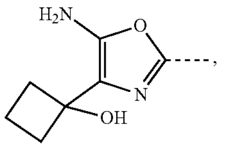
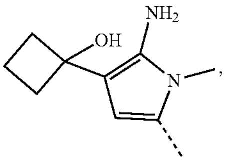
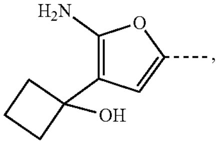
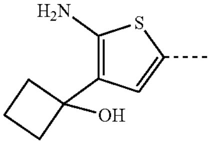
and
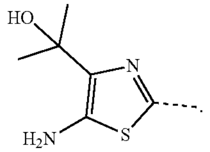

18. The compound or the pharmaceutically acceptable salt thereof according to claim 1, selecting from, (I-5)

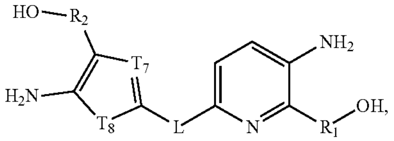

(I-6)

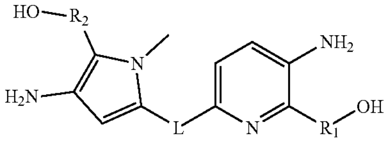
and

-continued
(P-1)
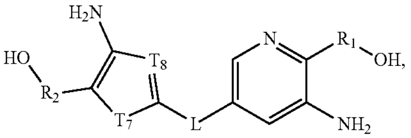
wherein,
$T_7$ is selected from N and $CR_3$;
$T_8$ is selected from O and S;
$R_3$ is selected from H, F, Cl, Br, I and $CH_3$;
$R_1$, $R_2$ and L are as defined in claim 1.
* * * * *